United States Patent
Bonrath et al.

(12) 
(10) Patent No.: US 6,444,098 B2
(45) Date of Patent: Sep. 3, 2002

(54) PROCESS FOR THE PREPARATION OF TOCOL ACYLATES AND TOCOPHEROL ACYLATES

(75) Inventors: Werner Bonrath, Freiburg (DE); Fabio Cirillo, Winterthur (CH)

(73) Assignee: Roche Vitamins Inc., Parsippany, NJ (US)

( * ) Notice: Subject to any disclaimer, the term of this patent is extended or adjusted under 35 U.S.C. 154(b) by 0 days.

(21) Appl. No.: 09/900,587

(22) Filed: Jul. 9, 2001

(30) Foreign Application Priority Data

Jul. 10, 2000 (EP) .............................................. 00114768

(51) Int. Cl.$^7$ .......................................... C07C 401/00
(52) U.S. Cl. .............................. 204/157.67; 204/157.69
(58) Field of Search ......................... 204/157.67, 157.69

(56) References Cited

U.S. PATENT DOCUMENTS 2,723,278 A    11/1955   Surmatis et al. ......... 260/345.5

FOREIGN PATENT DOCUMENTS

FR      2 666 581       3/1992
WO      WO 97/28151     8/1997

OTHER PUBLICATIONS

Bulychev, Technological Features of the Acetylation of alpha–Tocopherol, Khim.–Farm. Zh., vol. 32, No. 6, pp. 44–45. (month unavailable, 1998). Abstract only.*

D. Mingos and A. Whittaker, "Microwave Dielectric Heating Effects in Chemical Synthesis," chapter 11 of *Chemistry Under Extreme or Non–Classical Conditions*, Ed. R. Van Eldik and C. Huibbard, Wiley, New York (1996) Month Unavailable.

N. Cohen, et al., "Total Synthesis of All Eight Stereoisomers of α–Tocopherol Acetate. Determination of Their Diastereoisomeric and Enantiomeric Purity by Gas Chromatography," *Helvetica Chimica Acta.*, vol. 64, pp. 1158, 1172 (1981) month unavailable.

Lin and Lin, "Microwave–Promoted Lipase–Catalyzed Reactions," *Tetrahedron Letters*, vol. 39, pp. 4333–4336 (1998) Month Unavailable.

Herradón, et al., "Microwave Accelerated Organic Transformations: Dibutylstrannylene Acetal Mediated Selective Acylation of Polyols and Amino Alcohols Using Catalytic Amounts of Dibutyltin Oxide. Influence of the Solvent and the Power Output on the Selectivity," *Synlett*, No. 5, pp. 455–458 (1995) month unavailable.

Morcuende, et al., "Microwave–Promoted Transformations: Fast and Chemoselective N–Acylation of Amino Alcohols Using Catalytic Amounts of Dibutyltin Oxide. Influence of the Power Output and the Nature of the Acylating Agent on the Selectivity," *J. Org. Chem.*, vol. 61, pp. 5264–5270 (1996) month unavailable.

Derwent English language abstract of FR 2 666 581 (document B2 above) 3/92.

* cited by examiner

Primary Examiner—Edna Wong
(74) Attorney, Agent, or Firm—Bryan Cave LLP

(57) ABSTRACT

The present invention relates to a process for preparing tocol acylate or tocopherol acylate having the following steps:
  a) combining tocol or tocopherol with an acylating agent to form a reaction mixture;
  b) irradiating the reaction mixture with microwave energy to from tocol acylate or tocopherol acylate; and
  c) isolating the tocol acylate or tocopherol acylate from the reaction mixture.

20 Claims, No Drawings

PROCESS FOR THE PREPARATION OF TOCOL ACYLATES AND TOCOPHEROL ACYLATES

FIELD OF THE INVENTION

The present invention relates to a process for the preparation of tocol acylates and tocopherol acylates.

BACKGROUND OF THE INVENTION

The synthesis of (all-rac)-α-tocopherol acetate starting from acetic anhydride and (all-rac)-α-tocopherol, without a catalyst, in an excess of acetic anhydride has been reported by Surmatis et al., U.S. Pat. No. 2,723,278. The mixture was refluxed for three hours to form the product. The yield was not reported. This reaction can also be carried out in the presence of pyridine (as a catalyst) at room temperature to yield, after a reaction time of three days, 96% (all-rac)-α-tocopherol acetate. See Cohen et al., Helv. Chim. Acta 1981, 64, 1158.

SUMMARY OF THE INVENTION

The present invention relates to a process for the preparation of tocol and tocopherol acylates, more particularly tocopherol acetates. The main commercial form of vitamin E being (all-rac)-α-tocopherol acetate, the invention, in a preferred embodiment, provides a process for the preparation of (all-rac)-α-tocopherol acetate. However, other tocopherols can be readily acylated by the process of the present invention. Further, by the process of the instant invention, the tocopherols can be acylated in the form of their racemates or individual enantiomers.

One embodiment of the present invention is a process for preparing tocol acylate or tocopherol acylate having the following steps:
  a) combining tocol or tocopherol with an acylating agent to form a reaction mixture;
  b) irradiating the reaction mixture with microwave energy to form tocol acylate or tocopherol acylate; and
  c) isolating the tocol acylate or tocopherol acylate from the reaction mixture.

Another embodiment of the present invention is a process for preparing tocopherol acylate having the following steps:
  a) combining tocopherol and an acylating agent to form a reaction mixture;
  b) exposing the reaction mixture to microwave energy at about 600 to about 1200 watts; and
  c) recovering the tocopherol acylate from the reaction mixture.

A further embodiment of the present invention is a process for preparing tocol acylate or tocopherol acylate having the following steps:
  a) providing a reaction mixture consisting essentially of tocol or tocopherol and an acylating agent;
  b) irradiating the reaction mixture with microwave energy to form tocol acylate or tocopherol acylate; and
  c) isolating the tocol acylate or tocopherol acylate from the reaction mixture.

DETAILED DESCRIPTION OF THE INVENTION

In accordance with the present invention it has been found that the acylation of tocol and tocopherols can advantageously be effected under irradiation with microwaves. As compared to prior art processes, the process of the present invention requires shorter reaction time, gives better yield, and has a simpler work-up of the reaction mixture. In particular, the process of this invention does not require external heating of the reaction mixture, thus providing uniform reaction conditions throughout the entire reaction mixture.

The present invention is process for preparing tocol acylate or tocopherol acylate having, the following steps:
  a) combining tocol or tocopherol with an acylating agent to form a reaction mixture;
  b) irradiating the reaction mixture with microwave energy to from tocol acylate or tocopherol acylate; and
  d) isolating the tocol acylate or tocopherol acylate from the reaction mixture.

The present invention also provides a process for preparing tocopherol acylate having the following steps:
  a) combining tocopherol and an acylating agent to form a reaction mixture;
  b) exposing the reaction mixture to microwave energy at about 600 to about 1200 watts; and
  c) recovering the tocopherol acylate from the reaction mixture.

Tocol is the compound 2-methyl-2(4,8,12-trimethyl-tridecyl)-chroman-6-ol. The term "tocopherol" as used herein means all the compounds derived from the basic structure of tocol and having vitamin E character, such as, for example, the tocopherols having a saturated (tocol) side chain, such as α-, β-, γ-, δ-, $\zeta_2$- and η-tocopherol, and the tocotrienols having three double bonds in the side chain such as ε- and $\zeta_1$-tocopherol. Of the various tocopherols, (all-rac)-α-tocopherol (generally referred to as vitamin E) is preferred.

The term "microwave" as used herein refers to the region of the electromagnetic spectrum having frequencies of 30 GHz to 300 MHz, thus corresponding to wavelengths of 1 cm to 1 m. In order not to interfere with wavelengths for Radar (1 cm–25 cm), household or industrial microwave heaters are required to operate at either 12.2 cm (2.45 GHz) or 33.3 cm (918 MHz). Thus, in a preferred embodiment of the invention, the term microwaves refers particularly to such wavelengths. In the process of this invention, conventional microwave equipment can be used. Microwave equipment suitable in the process of this invention is readily available, e.g., MLS, Leutkirch, Germany (Lavis Multiquant 1000); or MILESTONE Inc., Monroe, Conn. 06468, USA (Ethos reactors). Conveniently, the irradiation in the process of this invention is carried out by applying a power of irradiation of from about 600 to about 1200 W, more preferably from about 800 to about 1000 W.

The acylation can be carried out using any acylating agent conventionally used for the acylation of a phenolic hydroxy group as is present in tocol and tocopherols, e.g., acyl anhydrides or halogenides. The acyl groups in such acylating agent may be derived from aliphatic carboxylic acids, e.g., from alkanoic acids, in particular C1–7 -alkanoic acids such as acetic acid, propionic acid, butyric acid, or pivalic acid, or higher alkanoic acids, such as palmitic acid; or from aromatic carboxylic acids, e.g., benzoic acid; or araliphatic acids, e.g. phenylacetic acid.

The acylation can be carried out in the presence or in the absence of a catalyst such as an organic base, e.g. pyridine or dimethylamino pyridine, or an organic or inorganic acid, e.g., sulfuric acid or p-toluenesulfonic acid. Advantageously, if a catalyst is used, a volatile catalyst is selected. In a preferred embodiment of this invention, the acylation is carried out in the absence of a catalyst. The acylating agent is suitably used in excess, i.e. in an excess of about 100% over the stoichiometrically required amount. Suitably, the reaction is carried out in an inert atmosphere. The desired tocol acylate or tocopherol acylate can be isolated from the reaction product by conventional means, e.g., by heating the reaction mixture under reduced pressure to remove excess acylating agent and catalyst, if any, and other unwanted products. While the process of the present invention is preferably concerned with the acylation of (all-rac)-tocopherols, particularly (all-rac)-α-tocopherol, the process can also be used to acylate optically pure enantiomers, such as (d-)-α-tocopherol.

The following examples are provided to further illustrate the process of the present invention. These examples are illustrative only and are not intended to limit the scope of the invention in any way.

EXAMPLES

Example 1

(All-rac)-α-Tocopherol (52.63g, 95% pure, corresponding to 116 mmol) and acetic anhydride (22.69 ml; 242 mmol) were placed in a flask. Pyridine catalyst (0.31ml, 3.9 mmol) was immediately added to the reaction mixture. The reaction mixture was stirred and irradiated with 800 W or 1000 W microwaves using a LAVIS Multiquant reactor under an inert gas atmosphere (Argon). The reaction product obtained was purified by heating to 70° C. under 25 mbar. The residue was analyzed by gas chromatography (GC) (XTI-5, 30m×0.32 mm, Film 0.25 mm, fused silica; 150° C. (0 min) 5° C./min 335° C. (8 min), He 2.0 ml/min) against an internal standard (1.0 g octacosan in 100 ml n-heptane). The conversion of the tocopherol to its acetate after 5, 10, 20 and 30 minutes is shown in Tables 1 and 2 below. (Deviations in the sum of the percentages from 100 are due to analytical errors.)

TABLE 1

Conversion of tocopherol to tocopherol acetate; catalyst present; irradiation at 800 W

| Time (in minutes) | 5 | 10 | 20 | 30 |
|---|---|---|---|---|
| tocopherol acetate [%] | 43 | 94 | 99 | 99 |
| tocopherol [%] | 48 | 0 | 0 | 0 |

TABLE 2

Conversion of tocopherol to tocopherol acetate; catalyst present; irradiation at 1000 W

| Time (in minutes) | 5 | 10 | 20 | 30 |
|---|---|---|---|---|
| tocopherol acetate [%] | 98 | 98 | 100 | 100 |
| tocopherol [%] | 1 | 0 | 0 | 0 |

When carrying out the above reaction under conventional conditions (no irradiation, heating to 100° C.) 91% of tocopherol acetate and 0% of tocopherol were found in the reaction product after 30 minutes of reaction time.

Example 2

The acetylation of tocopherol was carried out using the procedure in Example 1, but in the absence of the catalyst (pyridine). The conversion of tocopherol to its acetate after 5, 10, 20 and 30 minutes is shown in Tables 3 and 4 below. (Deviations in the sum of the percentages from 100 are due to analytical errors.)

TABLE 3

Conversion of tocopherol to tocopherol acetate; no catalyst; irradiation at 800 W

| Time (in minutes) | 5 | 10 | 20 | 30 |
|---|---|---|---|---|
| tocopherol acetate [%] | 62 | 76 | 97 | 99 |
| tocopherol [%] | 37 | 24 | 3 | 1 |

TABLE 4

Conversion of tocopherol to tocopherol acetate; no catalyst; irradiation at 1000 W

| Time (in minutes) | 5 | 10 | 20 | 30 |
|---|---|---|---|---|
| tocopherol acetate [%] | 73 | 86 | 98 | 99 |
| tocopherol [%] | 27 | 14 | 2 | 2 |

When carrying out the above reaction under conventional conditions (no irradiation, no catalyst, reflux temperature, reaction time 3.5 hours) the conversion of tocopherol to its acetate proceeded as shown in Table 5 below (Deviations in the sum of the percentages from 100 are due to analytical errors.)

TABLE 5

Conventional conversion of tocopherol to tocopherol acetate (no catalyst)

| Time (in minutes) | 30 | 60 | 90 | 120 |
|---|---|---|---|---|
| tocopherol acetate [%] | 69 | 93 | 94 | 95 |
| tocopherol [%] | 30 | 9 | 6 | 5 |

The invention being thus described, it will be obvious that the same may be varied in many ways. Such variations are not to be regarded as a departure from the spirit and scope of the invention and all such modifications are intended to be included within the scope of the following claims.

What is claimed is:

1. A process for preparing tocol acylate or tocopherol acylate comprising:
   a) combining tocol or tocopherol with an acylating agent to form a reaction mixture;
   b) irradiating the reaction mixture with microwave energy to form tocol acylate or tocopherol acylate; and
   c) isolating the tocol acylate or tocopherol acylate from the reaction mixture.

2. A process according to claim 1 further comprising adding a catalyst to the reaction mixture prior to step b).

3. A process according to claim 2 wherein the catalyst is pyridine.

4. A process according to claim 1 wherein step a) is carried out with tocopherol.

5. A process according to claim 4 wherein the tocopherol is selected from the group consisting of the tocopherols having a saturated tocol side chain and the tocotrienols having three double bonds in the side chain.

6. A process according to claim 4 wherein the tocopherol is selected from the group consisting of (all-rac)-α-tocopherol, α-tocopherol, β-tocopherol, γ-tocopherol, δ-tocopherol, $\zeta_2$-tocopherol, η-tocopherol, ε-tocopherol and $\zeta_1$-tocopherol.

7. A process accordingly to claim 4 wherein the tocopherol is (all-rac)-α-tocopherol.

8. A process according to claim 1 wherein the acylating agent is an acetylating agent.

9. A process according to claim 8 wherein the acetylating agent is acetic anhydride.

10. A process according to claim 1 wherein the tocopherol is (all-rac)- -tocopherol, and the acylating agent is acetic anhydride.

11. A process according to claim 10 wherein the microwave energy is in the range of about 800 to about 1000 watts.

12. A process according to claim 1 wherein the microwave energy is in the range of about 600 to about 1200 watts.

13. A process according to claim 12 wherein the microwave energy is in the range of about 800 to about 1000 watts.

14. A process for preparing tocopherol acylate comprising:
   a) combining tocopherol and an acylating agent to form a reaction mixture;
   b) exposing the reaction mixture to microwave energy at about 600 to about 1200 watts; and
   c) recovering the tocopherol acylate from the reaction mixture.

15. A process according to claim 14 further comprising adding a catalyst to the reaction mixture prior to step b).

16. A process according to claim 15 wherein the catalyst is pyridine.

17. A process accordingly to claim 14 wherein the tocopherol is (all-rac)-α-tocopherol.

18. A process according to claim 14 wherein the acetylating agent is acetic anhydride.

19. A process according to claim 14 wherein the microwave energy is in the range of about 800 to about 1000 watts.

20. A process for preparing tocol acylate or tocopherol acylate comprising:
   a) providing a reaction mixture consisting essentially of tocol or tocopherol and an acylating agent;
   b) irradiating the reaction mixture with microwave energy to form tocol acylate or tocopherol acylate; and
   c) isolating the tocol acylate or tocopherol acylate from the reaction mixture.

* * * * *

UNITED STATES PATENT AND TRADEMARK OFFICE
CERTIFICATE OF CORRECTION

PATENT NO.   : 6,444,098 B2
DATED        : September 3, 2002
INVENTOR(S)  : Werner Bonrath and Fabio Cirillo It is certified that error appears in the above-identified patent and that said Letters Patent is hereby corrected as shown below:

<u>Column 5,</u>
Line 6, please change "(all-rac)- -tocopherol," to -- (all-rac)-α-tocopherol --;
Line 9, please change "in the range of about" to -- at about --;
Line 9, please change "to about" to -- or about --.

Signed and Sealed this

Seventeenth Day of December, 2002

JAMES E. ROGAN
*Director of the United States Patent and Trademark Office*